United States Patent
Howland et al.

(10) Patent No.: US 10,104,923 B2
(45) Date of Patent: Oct. 23, 2018

(54) WEARABLE SAFETY WARNING AND MEASUREMENT SYSTEM

(71) Applicant: Warwick Mills Inc., New Ipswich, NH (US)

(72) Inventors: Charles A. Howland, Temple, NH (US); John C. Howland, Cambridge, MA (US)

(73) Assignee: Warwick Mills Inc., New Ipswich, NH (US)

( * ) Notice: Subject to any disclaimer, the term of this patent is extended or adjusted under 35 U.S.C. 154(b) by 0 days.

(21) Appl. No.: 15/468,423

(22) Filed: Mar. 24, 2017

(65) Prior Publication Data

US 2017/0273374 A1   Sep. 28, 2017

Related U.S. Application Data

(60) Provisional application No. 62/312,490, filed on Mar. 24, 2016.

(51) Int. Cl.
    *A41D 19/00*    (2006.01)
    *A61B 5/01*    (2006.01)

(52) U.S. Cl.
    CPC ..... *A41D 19/0031* (2013.01); *A41D 19/0027* (2013.01); *A61B 5/01* (2013.01)

(58) Field of Classification Search
    CPC ... A41D 19/0031; A41D 19/0027; A61B 5/01
    See application file for complete search history.

(56) References Cited

U.S. PATENT DOCUMENTS

| 5,315,289 | A | 5/1994 | Fuller et al. |
| 2005/0017868 | A1 | 1/2005 | Yang |
| 2017/0248272 | A1 * | 8/2017 | Ullrich ...................... F16P 3/14 |

FOREIGN PATENT DOCUMENTS

| EP | 1086334 B1 | 2/2004 |
| KR | 1020140060917 A | 5/2014 |
| KR | 2020150001872 U | 5/2015 |

OTHER PUBLICATIONS

International Search Report and Written Opinion of PCT/US2017/024000, dated Jun. 5, 2017, 11 pages.

* cited by examiner

*Primary Examiner* — Leon Flores
(74) *Attorney, Agent, or Firm* — Maine Cernota & Rardin (57) ABSTRACT

An apparatus for protecting a power tool user includes a glove or other garment having at least one sensor that monitors proximity to the power tool. Glove embodiments can include finger and/or thumb proximity sensors, and/or sensors that detect hand position, finger and/or wrist joint angle, vibration, and/or acceleration. Sensing targets can be retroactively installed on the power tool, and can define warning and/or danger zones. Sensing can be via magnetic, electromagnetic, capacitive, eddy current, and/or range finding means. Sizes of warning and/or target areas can be controlled by selecting targets from a plurality of targets of various detection ranges. Protective responses can vary according to different sensed events, and can include audible, visual, and/or tactile alerts, and/or interruption of power to the tool. Embodiments can record proximity and/or status data during a work session for review, training, and certification purposes. A controller can be physically cooperative with the garment.

26 Claims, 6 Drawing Sheets

WEARABLE SAFETY WARNING AND MEASUREMENT SYSTEM

RELATED APPLICATIONS

This application claims the benefit of U.S. Provisional Application No. 62/312,490, filed Mar. 24, 2016, which is herein incorporated by reference in its entirety for all purposes.

FIELD OF THE INVENTION

The invention relates to power tool safety, and more particularly, to apparatus configured to enhance the safety of a user of power tools and to monitor the user's level of training.

BACKGROUND OF THE INVENTION

As portable and stationary power tools have become ubiquitous in manufacturing, construction and maintenance, so also have hand injuries that result from the use of power tools. Cut and puncture protective gloves, sleeves and aprons can be very effective against injuries arising from use of hand tools. However, the impact energies and strike rates of power tools are generally too high for personal protective equipment ("PPE") to be fully effective. Furthermore, in many cases, for example with rotary cutters and similar equipment, wearing of gloves and/or other PPE is not recommended, because some agencies feel that resulting snag and wind-up risks can make injuries more severe if such PPE becomes entangled in the rotary head.

One approach to reducing power tool injuries is to modify the power tools themselves in ways that reduce their risk. However, some users feel that such modifications can tend to interfere with tool operation. In addition, such safety modifications can be expensive. In particular, it can be prohibitively expensive for a machine shop or factory to replace an existing inventory of existing power tools with new power tools that include active sensors and other safety modifications and devices.

There is also a lack of standards for such safety devices and modifications, making it extremely unlikely that safety modifications would be consistent across an inventory of power tools purchased from multiple suppliers. As a result, such safety modifications and devices, if implemented on a full inventory of power tools, can impose a significant additional training burden on a machine shop or factory, in that users of the power tools must be trained in the operation of the safety features of each power tool, as well as in use of the tool itself.

What is needed, therefore, is an apparatus for protecting the hands of a power tool operator without imposing an undue cost and training burden on the owner of the power tool.

SUMMARY OF THE INVENTION

The present invention is an apparatus for protecting the hands of a power tool operator without imposing an undue cost and training burden on the owner of the power tool. The invention takes advantage of the fact that the key issue in protecting users from power equipment is training. When users are fully trained, they consistently keep their hands out of danger zones when using power tools. Conversely, the risk of injury is always greatest when new operators are being trained.

Accordingly, the present invention is an apparatus and method that protects the hands of a power tool operator while assisting in the operator's training. Embodiments of the disclosed apparatus can be adapted to existing power tools, further reducing the cost and providing for uniformity of the safety features across a full range of different power tools supplied by different manufacturers.

Specifically, the disclosed apparatus includes a garment with one or more integrated sensors, at least one target that is attached or attachable to a power tool and is detectable by the sensor, and a controller that monitors proximity of the sensor to the target and initiates a protective response when the sensor proximity is determined to be closer than a specified threshold distance. In various embodiments, the protective response can include one or more of an auditory, visual, and/or tactile alert (such as a vibrating device located near the sensor). In embodiments, the protective response includes cutting power to the power tool.

In embodiments, the garment further includes sensors that monitor directional and angular positional features of the user's body, accelerating movements of the user's body, and/or vibrations to which the user's body is subjected. Embodiments record and save measurements of position, movement, acceleration, linear and angular position, and vibration for later analysis, evaluation, certification, and training.

In embodiments, the disclosed garment is a glove that includes a set of sensors distributed over the hand(s) and fingers for measurement of tool proximity, finger and wrist joint angle, and hand and finger movement and acceleration. The disclosed glove system enables measurement of hand and finger proximity to blades and/or other dangerous elements of power tools.

In various embodiments, the garment is fashioned from a "smart textile," wherein the sensor or sensors are attached to the fabric or embedded within the fabric, and the interconnections between the sensor or sensors and the controller are provided by conductors that are integral with the fabric.

Embodiments of the invention enable the predefinition of danger and/or warning zones surrounding dangerous elements of a power tool. In some of these embodiments, the warning and danger zones are delimited by placement of targets at selected locations surrounding the dangerous elements. In various embodiments, a plurality of different types of target are provided, so as to enhance the ability of the sensor(s) to determine positional information relative to the power tool and defined zones. Some embodiments further enable specification of appropriate protective responses depending on the nature of an alert. For example, in embodiments a perceptible warning such as an audible alarm is initiated when a glove sensor enters a defined warning zone, while the power to the tool is cut off if the sensor enters a defined danger zone.

In some embodiments, the controller is attached to or integral with the glove or other garment. In other embodiments, the controller is a separate unit. Communication between the sensor(s), controller, alert-generating devices, data logging units, and/or the power supply of the power tool can be by any combination of wired and wireless means known in the art, including Bluetooth and USB connections.

It will be understood by one of skill in the art that while much of the present disclosure is described with reference to a glove, the disclosure applies equally to other parts of a user's body, such as a foot, elbow, or knee, that interact with or otherwise are subject to coming into contact with dangerous aspects of a power tool. In such cases a shoe, elbow pad, knee pad, etc. is substituted in place of the glove described herein.

A first general aspect of the present invention is an apparatus for enhancing safety of a power equipment user. The apparatus includes a garment, at least one proximity measurement sensor cooperative with the garment, a control system in communication with the proximity measurement sensor, and a responding system cooperative with the control system and configured to provide a protective response when specified conditions are detected by the control system based on measurements made by the at least one proximity measurement sensor.

In embodiments, the protective response includes a warning signal that is perceptible to the power equipment user.

In some of these embodiments, the perceptible warning signal includes at least one of a visible warning signal, an audible warning signal, and a vibrational warning signal.

In any of the above embodiments, the protective response can include terminating delivery of power to the power equipment.

Any of the above embodiments can further include a logging system configured to log data obtained by the apparatus.

In any of the above embodiments, the garment can include a piezo thin film laminate sensor and/or a piezo fiber strain sensor.

In any of the above embodiments, the garment can be a glove, and the at least one proximity measurement sensor can include a sensor that is cooperative with a fingertip of the user. Some of these embodiments include sensors that are cooperative with an index finger of the user, a smallest figure of the user, and a thumb of the user.

In any of the above embodiments, the at least one proximity measurement sensor can be configured to sense at least one of a magnetic field and an eddy current.

In any of the above embodiments, the at least one proximity measurement sensor can be at least one of capacitive and inductive.

In any of the above embodiments, the at least one proximity measurement sensor can be a range finding sensor.

In any of the above embodiments, the at least one proximity measurement sensor can be configured to measure an electromagnetic spectrum.

Any of the above embodiments can further include a target that is cooperative with the power equipment and can be sensed by the at least one proximity measurement sensor. Some of these embodiments include a plurality of targets that can be selected so as to define at least one of a warning region and a danger region associated with the power equipment. In any of these embodiments, the target or targets can be configured for retrofit attachment to the power equipment.

Any of the above embodiments can further include a status sensor that is configured to measure at least one of position, angular joint configuration, acceleration, and vibration.

And in any of the above embodiments, the control system can be physically cooperative with the garment.

A second general aspect of the present invention is a garment that includes a sensor and a logging system that is in data communication with the sensor, the sensor and data system being configured to record data pertaining to at least one of proximity of said garment to a designated location, a skin temperature of a user, a finger angle of the user, and a wrist joint angle of the user.

In any of the above embodiments, the logging system can be configured to execute an algorithm that permits subsequent display of the recorded data. And in some of these embodiments, the algorithm permits subsequent display of the recorded data as a function of time.

A third general aspect of the present invention is a garment configured for wearing by a user, the garment comprising a sensing system and a responding system, the responding system being configured to provide at least one of an optical signal to the user, a vibrational signal to the user, an acoustic signal to the user, and an electrical signal to the equipment.

A fourth general aspect of the present invention is a sensing system and a garment controller in communication with an external power equipment control system, said garment controller being configured to deactivate said power equipment according to measurements made by the sensing system.

In embodiments, the garment controller is in wireless communication with the external control system. In some of these embodiments, the wireless communication is Bluetooth communication.

In any of the above embodiments, the garment controller can be in wired communication with the external control system.

And in any of the above embodiments, the garment can be controlled by a control panel that is attached to the garment.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Proximity Sensing Mode

As noted above, the present invention is an apparatus for protecting the hands (or other body parts) of a power tool operator. Embodiments reduce the cost to a machine shop or other multi-tool facility by taking advantage of the fact that the key issue in protecting users from power equipment is training.
Accordingly, embodiments of the disclosed apparatus provide features that directly assist with training, evaluating, and certifying new users of power tools, such that extraordinary safety devices and modifications need not be implemented on power tools that are only used by experienced operators.

Furthermore, embodiments of the present invention can be adapted to existing power tools, further reducing the cost and providing for uniformity of the safety features across a full range of different power tools supplied by different manufacturers. Some of these embodiments require only that passive modifications be applied to existing power tools. Such modifications can be simple for users to make and enable the retrofitting of power tools that have already been purchased. In embodiments, these passive modifications include the mounting by users on the power equipment of magnetic, optical, and/or capacitive targets that can be selected from a set of targets supplied with the disclosed system. The mounting can be adhesive or via any attachment means known in the art.

Figure 1:
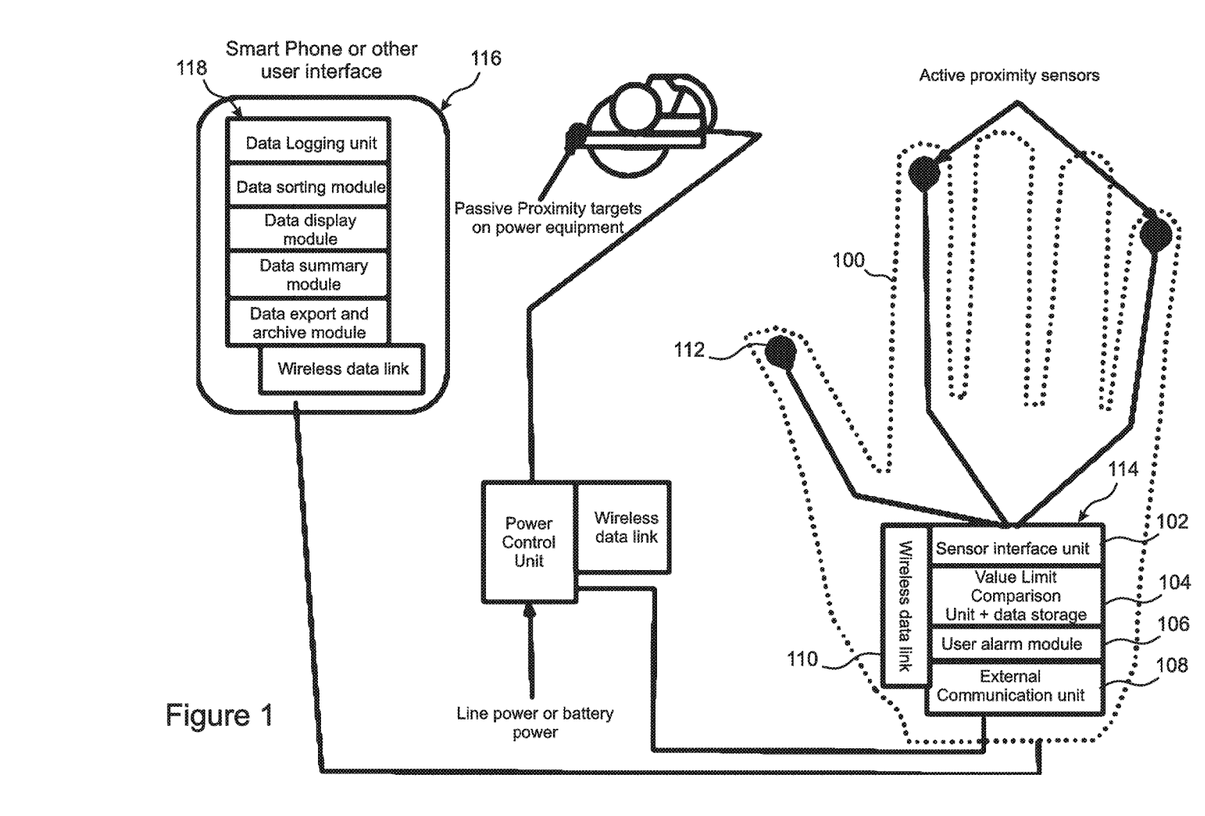
FIG. 1 is a block diagram illustrating an embodiment of the present invention.

With reference to FIG. 1, in embodiments the disclosed apparatus of the present invention includes a wearable glove 100 or other garment that includes at least one sensor 112 and a controller 114. In the embodiments of FIG. 1, the controller 114 is attached to the glove 100, while in similar embodiments the controller is separate from the garment 100 and in wired or wireless communication therewith.

In embodiments, the controller 114 includes the following five functional elements:
1) a sensor interface unit 102;
2) a value limit comparison unit and data logger 104;
3) a user alarm module 106;
4) a external communication unit 108; and
5) a wireless data link 110.

In some embodiments, all of these functional elements are provided by a single microprocessor-based machine controller 114. In various embodiments, the sensor interface unit 102 is designed to interface with redundant sensors that reduce the potential for a false negative result. In these embodiments, the risk of a false positive is very low, because the only action taken by the system in the case of a false alert is to issue a perceptible warning and/or shut down the power equipment. This is in contrast to some integrated safety systems of the prior art that use a high speed actuator to stop a blade or tool cutter, such that a false safety alert can damage the equipment such that it must be repaired, and a new cutter must be mounted, before the equipment can be used again. Accordingly, because the penalty incurred as a result of a false safety alert is only a small loss in productivity, embodiments of the present invention bias sensor and value limit comparison thresholds to be conservative, thereby limiting risk to the operator.

Work Piece Hand Axis and Tool and Workpiece Axis of Travel

Figure 2A:
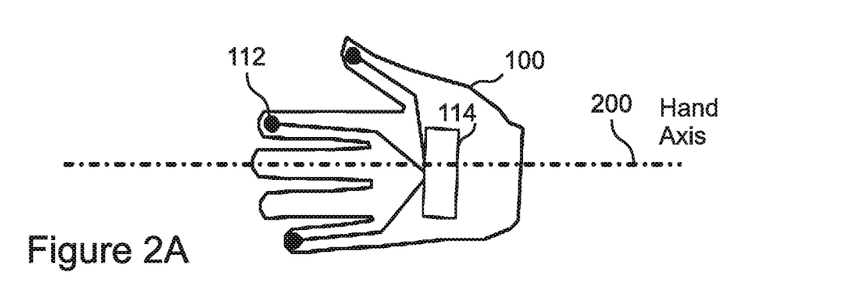
FIG. 2A illustrates the definition of a hand axis included in a coordinate system that is used to describe embodiments of the present invention.
Figure 2B:
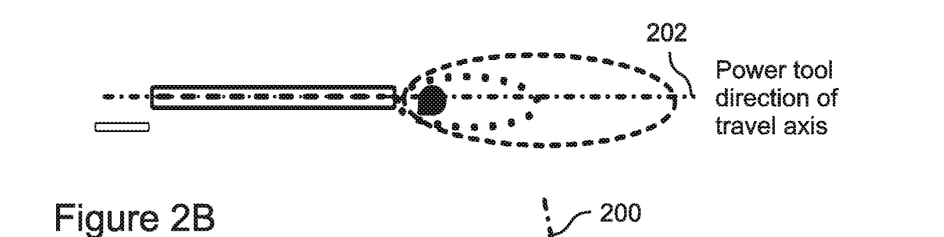
FIG. 2B illustrates the definition of a tool axis included in a coordinate system that is used to describe embodiments of the present invention.
Figure 2C:
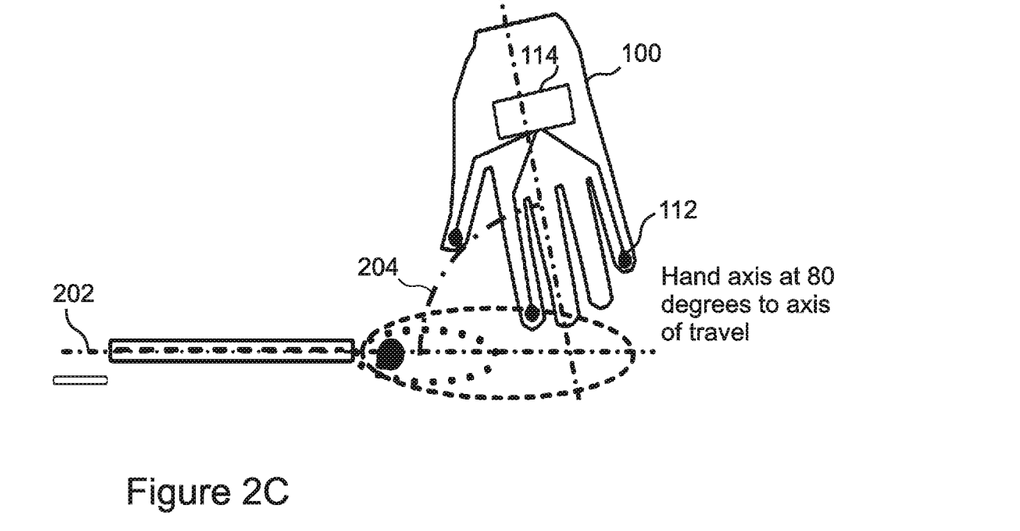
FIG. 2C illustrates the definition of an angle between the hand axis and the tool axis in a coordinate system that is used to describe embodiments of the present invention.

With reference to FIGS. 2A through 2C, a coordinate system for the description of the axis of a hand 200 and a sensor axis 202 are defined. This reference frame is used herein to describe the geometry of embodiments of glove sensors 112, including their sensitivity and the corresponding target sensitivity. As shown in FIG. 2C, the angle 204 referred to in the following description is taken from the small finger side of the glove 100 to the tool or work piece axis.

Proximity Sensor Alignment to Tool or Workpiece Travel Direction

Figure 3A:
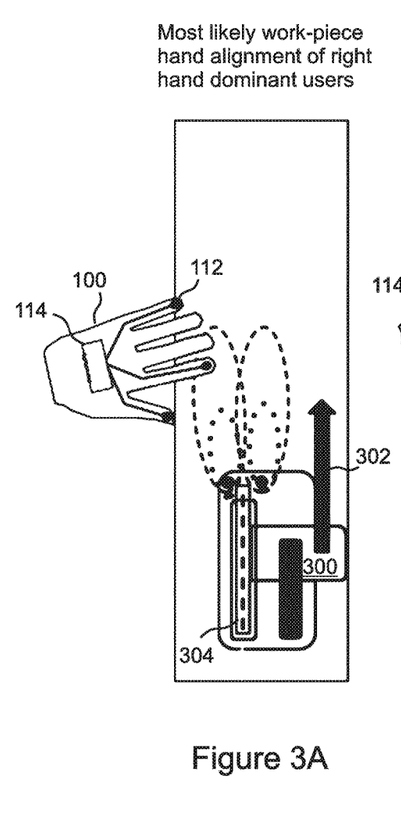
FIG. 3A illustrates the most likely work-piece hand alignment relative to power equipment of a right hand dominant user.
Figure 3B:
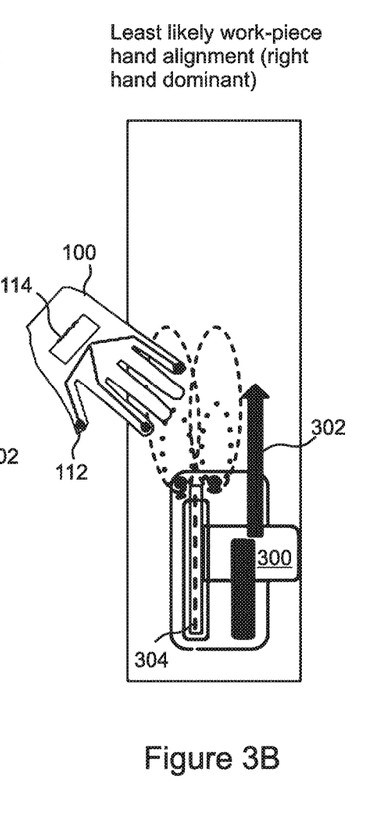
FIG. 3B illustrates the least likely work-piece hand alignment relative to power equipment of a right hand dominant user.
Figure 3C:
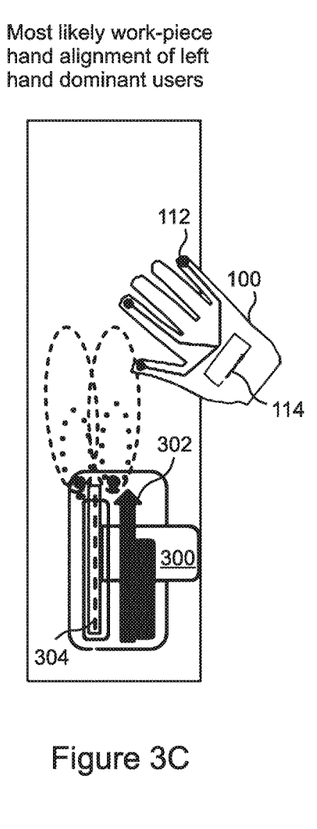
FIG. 3C illustrates the most likely work-piece hand alignment relative to power equipment of a left hand dominant user.

As can be seen from FIGS. 3A and 3C, the most likely alignment of hand 100 closest to a work-piece 300 is approximately perpendicular to the direction of travel 302 of the power tool 302. With reference to FIG. 3B, as the alignment of the work-piece hand 100 goes beyond 90 degrees to the direction of travel 300, this results in upper arm and shoulder strain for the operator, so this configuration is not very likely. In embodiments, the sensitivity direction of the proximity sensors 112 is aligned approximately 80 degrees from perpendicular to the hand axis 200. This configuration maximizes the signal in the most likely work-piece hand alignments relative to the direction of tool travel 300.

Thumb and Small Finger Sensing Configurations

Figure 4A:
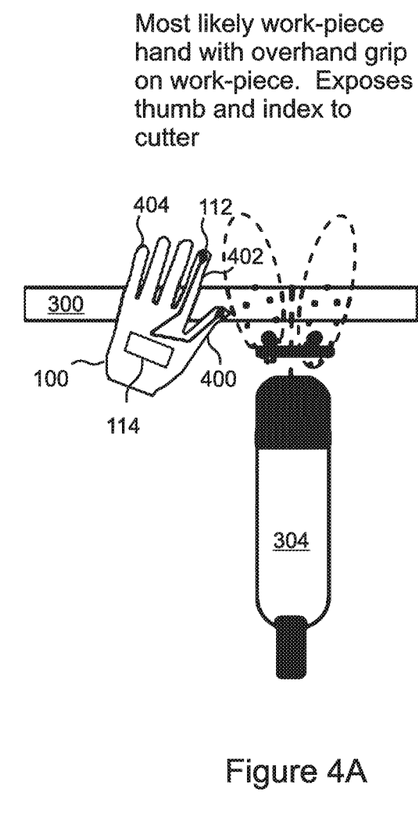
FIG. 4A is a side view of the most likely work-piece hand position when in an overhand grip on the work-piece.
Figure 4B:
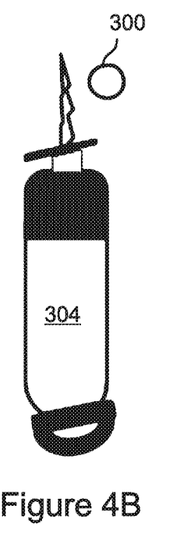
FIG. 4B is an end view of the position of FIG. 4A.
Figure 4C:
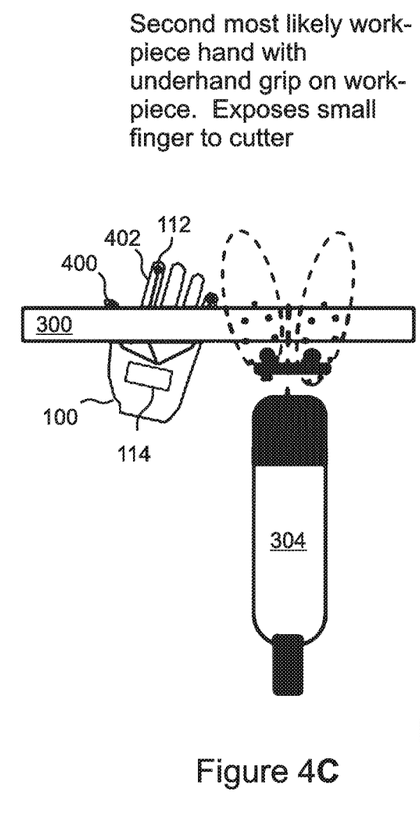
FIG. 4C is a side view of the second most likely work-piece hand position when in an underhand grip on the work-piece.
Figure 4D:
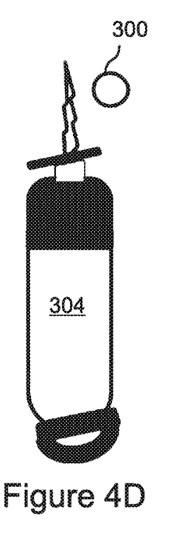
FIG. 4D is an end view of the position of FIG. 4C.

With reference to FIG. 4A, in many cases when an accident does occur, the most likely affected parts of the hand 100 are the thumb 400 and index finger 402. Accordingly, in the embodiment of FIG. 4A, sensors 112 are included only in these two locations. With reference to FIG. 4B, the small finger 404 is at risk only in the less likely, underhand work holding position. Accordingly, in the embodiment of FIG. 4B, the sensors 112 are distributed only in the thumb, index, and small finger regions to protection the work-piece hand in the underhand work holding position.

Stationary Power Tool Proximity Configurations

Figure 5A:
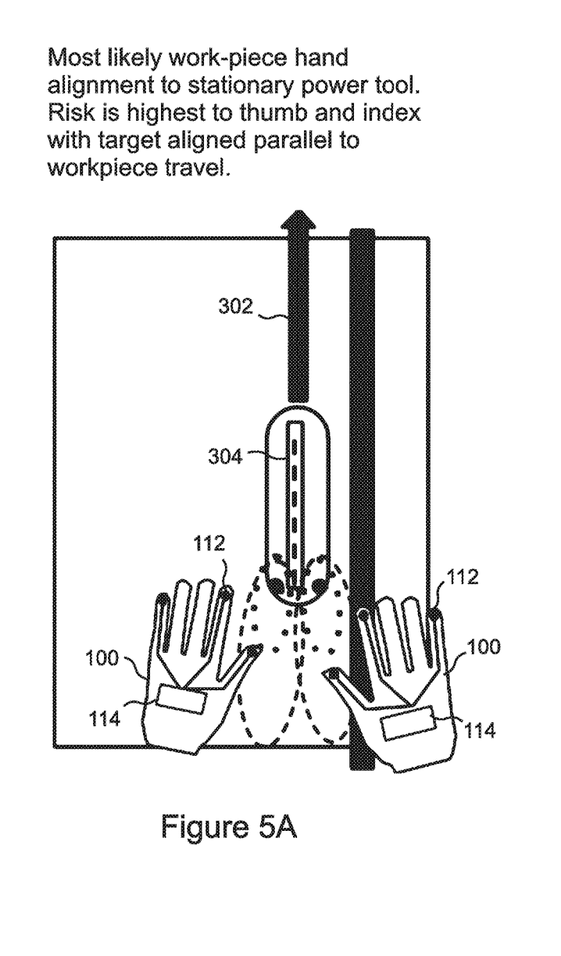
FIG. 5A illustrates the most likely work-piece hand alignment to a stationary power tool.
Figure 5B:
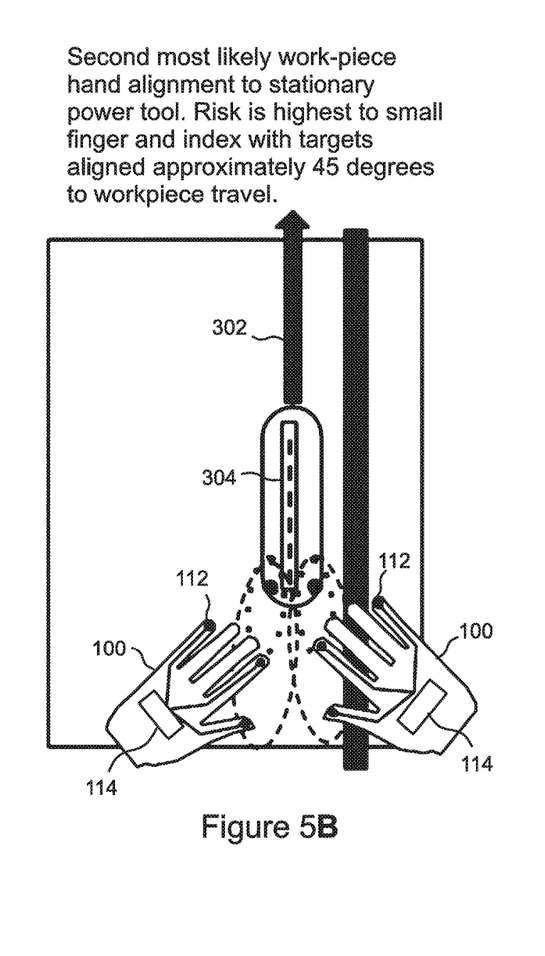
FIG. 5B illustrates the second most likely work-piece hand alignment to a stationary power tool.

With reference to FIGS. 5A and 5B, in some embodiments the sensitivity directions of the sensors 112 in the gloves 100 are configured to include 45 degree alignment 204 between the hand axis 200 and the direction of travel 302.

Proximity Sensors

Figure 6:
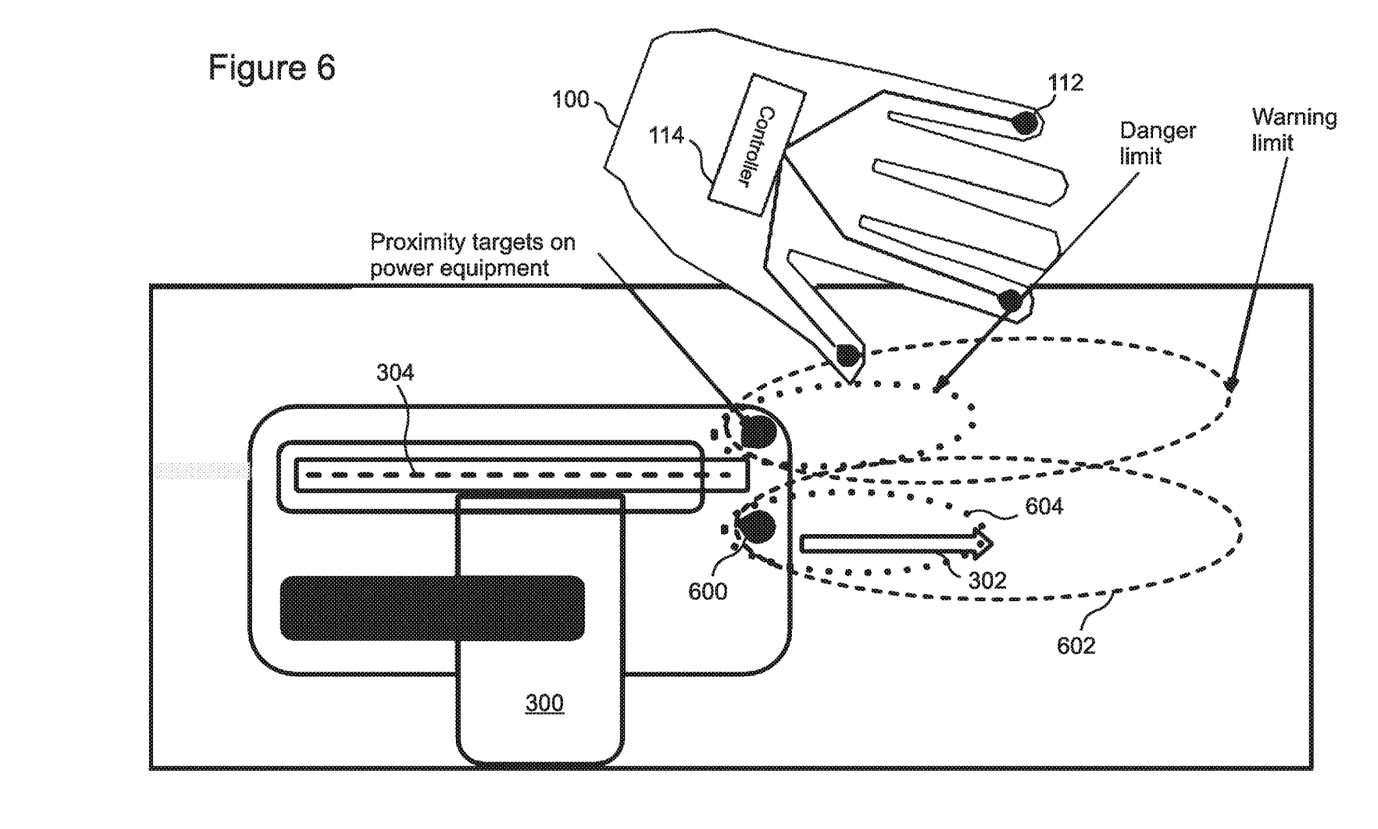
FIG. 6 illustrates interaction between sensors in fingertips of a glove and proximity targets located on power equipment.

With reference to FIG. 6, in certain embodiments the system of the present invention makes use of magneto-inductive sensors (MIS) 112 and interchangeable, permanent magnet targets 600. Some of these embodiments provide target magnets 600 that are interchangeable on the power equipment. In embodiments, a magnet set is selected from among a group of magnet sets according to the size and configuration of the power tool, the level of experience of the user, and other factors, wherein each magnet set provides a different combination of magnet strengths. This allows the strengths of the magnetic fields, and hence the sensing distance from the glove sensor 112 to the equipment 600, to be changed simply by changing to a different set of magnets.

This approach makes it easy to adjust warning 602 and danger 604 standoff distances simple by exchanging the magnetic targets 600. Accordingly, in these embodiments there is often no need to adjust the sensing limits in the value limit comparison unit 104. Instead, the user makes these changes simply by exchanging the magnetic targets 600.

Safety Control Mode

For some institutions and companies the desired mode for safety is to require the use of safety gloves 100 during operation of power equipment. To support this operating mode, embodiments of the present invention include lockable plugin bases for all the controlled equipment. The lockable plugin bases are configured such that when they are present, the power to the equipment is not enabled unless the safety gloves 100 are worn. In certain of these embodiments, the proximity sensing is in place and continues to shut off power when the hands are found to be in the danger zone 604.

Vibration Measurement

Embodiments of the present invention combine measurement of power tool proximity with sensing of induced vibration in the hands from the power tool. Hand Arm Vibration Syndrome, or "HAVS," is considered to be an occupational injury, and so it can be desirable to accumulate data that documents the actual vibration exposure and durations experienced by a power tool user. Accordingly, embodiments of the present invention are able to alert the user when preset vibration limits are exceeded.

Both the warning to the user and the accumulated vibration data can be useful in modifying behavior to help configure the work environment to produce safer, lower vibration impact to the user's hands. The starting point for these limit values is the British HSE values of 2.5 m/sec 2 warning limit and 5 m/sec 2 damage limit. The data logging function in some of these embodiments is also useful in allowing the employer to audit and document the vibration impact from a task. In some embodiments, the measurements made by the system are modeled after ANSI 2.70 and ISO53491 2001, which can be found at https://www.aiha.org/LocalSections/html/florida/AIHA%20FL%200509%20rev1C.pdf, incorporated herein by reference for all purposes.

Repetitive Motion and Forces and Impact Measurement

Embodiments include motion and acceleration sensors that can be used to monitor and warn against injury due to repetitive motions, forces, and impacts. The measured data can be compared with established criteria, such as the US CDC criteria that can be found at http://www.cdc.gov/niosh/docs/97141/pdfs/97141e.pdf, which is incorporated herein by reference for all purposes.

Training Mode

With reference again to FIG. 1, in embodiments of the present invention, in addition to providing warnings to the user and power interruptions in response to proximity of the sensors to the danger zone 604 of the equipment, the on-garment controller 114 also logs data over a session, and this data is provided to an external display and analysis system such as a smart phone 116 or computer. In various embodiments, the analysis system 116 includes a data base structure 118 that logs user names, start and end times for a session, as well as the type of task, work cell, and or equipment types the user was operating during the data collection session. This data can then be used by employers and/or school personnel to evaluate the level of proficiency of the user. In embodiments, the data includes the number of events where the user's hands were in the warning area 602, and the number of events when the user's hands were in the danger zone 604, causing the equipment power to be cut.

Embodiments include a vibration mode, in which the magnitudes and durations of exposure of the user's hands to vibrations are recorded.

Various embodiments include a joint angle and impact mode, in which flex events are logged and the number of over-flex events and hyper-flex events are logged.

Certain embodiments include a productivity mode, in which the flex and vibration patterns are logged, so that by using pattern learning or other forms of pattern recognition the total number of relevant events can be determined. Deviation from the ideal task flex and vibration patterns can be assessed, and data-driven training can be used to help operators improve safety and performance.

Various embodiments include an analysis function that permits a school or employer to set criteria for maximum numbers and types of incursions into warning zones 602 and danger zones 604 that are allowed for safe qualification of an operator on a task that requires use of a piece of equipment or work cell. In such instances, the operating data provided by embodiments of the present invention can be very useful for schools and/or employers who need evidence that training has been effective.

The use of the training mode in embodiments integrates very well with behavioral safety programs. For example, when new operators have used the data logging system 118 over enough sessions to demonstrate that they have internalized the safe working positions for their hands, the operator can be qualified on the task. After that, the training mode need only be used again for periodic audits of operator behavior.

The foregoing description of the embodiments of the invention has been presented for the purposes of illustration and description. Each and every page of this submission, and all contents thereon, however characterized, identified, or numbered, is considered a substantive part of this application for all purposes, irrespective of form or placement within the application.

This specification is not intended to be exhaustive. Although the present application is shown in a limited number of forms, the scope of the invention is not limited to just these forms, but is amenable to various changes and modifications without departing from the spirit thereof. One or ordinary skill in the art should appreciate after learning the teachings related to the claimed subject matter contained in the foregoing description that many modifications and variations are possible in light of this disclosure. Accordingly, the claimed subject matter includes any combination of the above-described elements in all possible variations thereof, unless otherwise indicated herein or otherwise clearly contradicted by context. In particular, the limitations presented in dependent claims below can be combined with their corresponding independent claims in any number and in any order without departing from the scope of this disclosure, unless the dependent claims are logically incompatible with each other.

We claim:

1. An apparatus for enhancing safety of a power equipment user, the apparatus comprising: a glove; at least one proximity measurement sensor cooperative with the glove; a target that is cooperative with the power equipment and can be sensed by the at least one proximity measurement sensor, said target having a field, emission, absorption, or reflectivity that is detectable by the proximity measurement sensor and is absent from all nearby structures that are not targets; a control system in communication with the proximity measurement sensor; and a responding system cooperative with the control system and configured to provide a protective response when specified conditions are detected by the control system based on measurements made by the at least one proximity measurement sensor.

2. The apparatus of claim 1, wherein the protective response includes a warning signal that is perceptible to the power equipment user.

3. The apparatus of claim 2, wherein the perceptible warning signal includes at least one of:
 a visible warning signal;
 an audible warning signal; and
 a vibrational warning signal.

4. The apparatus of claim 1, wherein the protective response includes terminating delivery of power to the power equipment.

5. The apparatus of claim 1, further comprising a logging system configured to log data obtained by the apparatus.

6. The apparatus of claim 1, wherein the glove includes a piezo thin film laminate sensor.

7. The apparatus of claim 1, wherein the glove includes a piezo fiber strain sensor.

8. The apparatus of claim 1, wherein the at least one proximity measurement sensor includes a sensor that is cooperative with a fingertip of the glove.

9. The apparatus of claim 1, wherein the at least one proximity measurement sensor includes: a sensor that is cooperative with an index finger of the glove; a sensor that is cooperative with a smallest finger of the glove; and a sensor that is cooperative with a thumb of the glove.

10. The apparatus of claim 1, wherein the at least one proximity measurement sensor is configured to sense at least one of a magnetic field and an eddy current.

11. The apparatus of claim 1, wherein the at least one proximity measurement sensor is at least one of capacitive and inductive.

12. The apparatus of claim 1, wherein the at least one proximity measurement sensor is a range finding sensor.

13. The apparatus of claim 1, wherein the at least one proximity measurement sensor is configured to measure an electromagnetic spectrum.

14. The apparatus of claim 1, wherein the apparatus comprises a plurality of targets that can be selected so as to define at least one of a warning region and a danger region associated with the power equipment.

15. The apparatus of claim 1, wherein the target is configured for retrofit attachment to the power equipment.

16. The apparatus of claim 1, further comprising a status sensor that is configured to measure at least one of position, angular joint configuration, acceleration, and vibration.

17. The apparatus of claim 1, wherein the control system is physically cooperative with the glove.

18. The apparatus of claim 1, further comprising a logging sensor and a logging system that is in data communication with the logging sensor, the logging sensor and the logging system being configured to record data pertaining to at least one of: proximity of the glove to the target; a skin temperature of a user; a finger angle of the user; and a wrist joint angle of the user.

19. The apparatus of claim 18, wherein the logging system is configured to execute an algorithm that permits subsequent display of the recorded data.

20. The apparatus of claim 19, wherein the algorithm permits subsequent display of the recorded data as a function of time.

21. A glove configured for wearing by a user, the glove comprising: a sensing system; a proximity sensor configured to sense proximity of the glove to a target that is cooperative with equipment, said target having a field, emission, absorption, or reflectivity that is detectable by the proximity sensor and absent from all structures proximal to the equipment that are not targets; and a responding system, the responding system being configured, when the proximity sensor of the sensing system senses proximity of the glove to the target to provide at least one of an optical signal to the user, a vibrational signal to the user, an acoustic signal to the user, and an electrical signal to the equipment.

22. A glove comprising: a sensing system that includes a proximity sensor configured to indicate proximity of the glove to a target that is cooperative with power equipment, said target having a field, emission, absorption, or reflectivity that is detectable by the proximity sensor and absent from all structures proximal to the equipment that are not targets; and a garment controller in communication with an external control system that is in control of said power equipment, said garment controller being configured to cause said external control system to deactivate said power equipment when measurements made by the proximity sensor of the sensing system indicate proximity of the glove to the target.

23. The glove of claim 22, wherein the garment controller is in wireless communication with the external control system.

24. The glove of claim 23, wherein the wireless communication is Bluetooth communication.

25. The glove of claim 22, wherein the garment controller is in wired communication with the external control system.

26. The glove of claim 22, wherein the garment controller is controlled by a control panel that is attached to the glove.

* * * * *